of Kanagawa, Japan

United States Patent [19]

Okumura et al.

[11] 3,960,571

[45] June 1, 1976

[54] SILVER HALIDE COLOR PHOTOGRAPHIC LIGHT-SENSITIVE MATERIAL

[75] Inventors: Akio Okumura; Yukio Yokota; Kozo Inouye; Keisuke Shiba; Minoru Yamada, all of Minami-ashigara, all of Kanagawa, Japan

[73] Assignee: Fuji Photo Film Co., Ltd., Minami-ashigara, Japan

[22] Filed: Sept. 27, 1974

[21] Appl. No.: 509,889

[30] Foreign Application Priority Data
Sept. 27, 1973 Japan.............................. 48-108798

[52] U.S. Cl................................ 96/100; 260/310 C
[51] Int. Cl.².......................................... G03C 1/40
[58] Field of Search....................................... 96/100

[56] References Cited
UNITED STATES PATENTS

| | | | |
|---|---|---|---|
| 3,580,722 | 5/1971 | Sakamoto et al. | 96/100 |
| 3,684,514 | 8/1972 | Iwama et al. | 96/100 |
| 3,761,274 | 9/1973 | Inoue et al. | 96/100 |
| 3,861,923 | 1/1975 | Hara et al. | 96/100 |

*Primary Examiner*—J. Travis Brown
*Attorney, Agent, or Firm*—Sughrue, Rothwell, Mion, Zinn & Macpeak

[57] ABSTRACT

A color photographic light-sensitive material having a silver halide emulsion layer containing a 1-phenyl-2-pyrazol-5-one magenta color-forming coupler, in which the 1-phenyl group of the coupler is substituted (1) with a $R_1OOC$-group, wherein $R_1$ represents a group having about 8 to 26 carbon atoms, or (2) with a $R_2OOC$-group and a $R_3OOC$-group, wherein $R_2$ and $R_3$, which may be the same or different, each represents a group having about 4 to 18 carbon atoms; and in which the 3-position of the pyrazolone is substituted with an acylamino group, an ureido group, an alkoxy group, an amino group or an anilino group. The color photographic light-sensitive material provides stable magenta dye images having good spectral absorption characteristics.

9 Claims, No Drawings

SILVER HALIDE COLOR PHOTOGRAPHIC LIGHT-SENSITIVE MATERIAL

BACKGROUND OF THE INVENTION

1. Field of the Invention

The present invention relates to a silver halide photographic light-sensitive material containing a novel magenta dye-forming coupler.

2. Description of the Prior Art

It is known that when a silver halide photographic light-sensitive material is exposed and color-developed, a coupler reacts with the oxidation product of an aromatic primary amino developing agent to produce an indophenol, indaniline, indamine, azomethine, phenoxazine, phenazine, or other similar dye, whereby a color image is formed. In such a system, color reproduction is achieved by a subtractive color process and yellow, magenta and cyan dye images corresponding to blue, green and red light images, respectively, are formed. In general, an acylacetamide coupler or a dibenzoyl methane coupler is used for forming a yellow color image, a pyrazolone coupler, a cyanoacetyl coupler or an indazolone coupler is used for forming a magenta dye image, and a phenolic coupler such as a phenol and a naphthol is used for forming a cyan color image.

In these color photographic processes, a dye-forming coupler is either added to a color developer solution or incorporated in a light-sensitive photographic emulsion. Thus, it is possible to react the coupler with the oxidation product of the color developing agent which is formed by developing a latent image during development.

Various kinds of 5-pyrazolone derivatives are known for forming magenta color images. For example, as substituents at the 3-position of the 5-pyrazolone ring, an alkyl group, an aryl group, an alkoxy group as described in U.S. Pat. No. 2,439,098, an acylamino group as described in U.S. Pat. Nos. 2,369,489 and 2,607,788, an ureido as described in U.S. Pat. No. 3,558,319, an anilino group as described in U.S. Reissue Pat. No. 22,329 and the like are known.

These couplers must be non-diffusible in order that these couplers are prevented from diffusing into other photographic emulsion layers having sensitivities to different spectral wavelength regions and mixing with other couplers to reduce the color reproducibility by causing color mixing when these couplers are used by incorporation into a silver halide photographic emulsion during the production of the photographic light-sensitive material. For this puprose, a hydrophobic residue containing about 8 or more carbon atoms, which contributes to a reduction in the diffusibility of the coupler, as a ballasting group, is introduced into the coupler molecule.

To incorporate non-diffusible couplers into a photographic emulsion, the following three methods have conventionally been used:

1. Aqueous solution system: A non-diffusible coupler having a water-solubilizing group such as a carboxyl group or a sulfo group and being soluble in an alkaline aqueous medium is incorporated into a photographic emulsion in the form of a neutral or alkaline aqueous solution thereof and then the emulsion is neutralized with an acid.

2. Oil solution system: A non-diffusible coupler is dissolved in an organic solvent, the solution is dispersed in an aqueous medium as fine colloidal particles, and the dispersion is added to a photographic emulsion.

3. A non-diffusible coupler is melted by heating and the melted coupler is directly dispersed in a photographic emulsion or an aqueous medium.

In order to produce a green-sensitive photographic emulsion layer having excellent properties using a coupler which forms a magenta dye image employing the oil solution system, the coupler must fulfill the following conditions: that is to say, the coupler must have a high coupling reactivity with the oxidation product of a color developing agent, the magenta dye image formed must have a high fastness so that the image can be stored under severe conditions without fading, the coupler must not adversely affect the photographic emulsion and further the coupler must be readily soluble in an organic solvent employed for dispersing the coupler in a photographic emulsion and crystallize to a lesser extent in the solvent.

However, conventionally known magenta dye-forming couplers in the oil solution system show insufficient reactivity with the oxidation product of the color developing agent in the dispersed state in a photographic emulsion layer. Thus, it is difficult to obtain a green sensitive emulsion layer having excellent photographic properties using the oil solution system.

Since a magenta dye image in a color photograph using the trichromatic subtractive color process absorbs light in a wave-length region where human visual sensitivity is the highest, the light absorption characteristics of the magenta dye image are a very important factor in determining the color reproduction properties of the color photograph. In particular, it has been believed desirable to improve the sharpness of the spectral absorption curve and to reduce the secondary absorption which is specific to a pyrazolone magenta coupler image and various efforts have been made in this respect.

Also, when conventional magenta dye images formed from various magenta dye image-forming couplers are stored under high temperature and humidity conditions for a long period of time, they tend to fade, and it has been desired to improve the fastness of the dye images.

SUMMARY OF THE INVENTION

An object of the present invention is to provide a magenta dye image-forming coupler suitable for producing a color photographic light-sensitive material using an oil solution system.

Another object of the present invention is to provide a color photographic light-sensitive material which can be used to produce clear colors by the subtractive color process.

Still another object of the present invention is to provide a color photograph which has a stable magenta dye image and which can be stored under severe conditions for a long period of time with less fading.

A further object of the present invention is to produce a color photographic light-sensitive material containing a magenta dye image-forming coupler which can be prepared easily using readily available raw materials.

Other objects of the present invention will become apparent from the following detailed description and examples as set forth below.

These objects are accomplished by incorporating, as a magenta dye image-forming coupler, a 1-phenyl-2-pyrazol-5-one derivative in which the 1-phenyl group is (1) substituted with a $R_1OOC$-group, wherein $R_1$ represents a group having about 8 to 26 carbon atoms, or (2) substituted with a $R_2OOC$-group and a $R_3OOC$-group wherein $R_2$ and $R_3$, which may be the same or different, each represents a group having about 4 to 18 carbon atoms, and the 3-position of the pyrazolone ring is substituted with an acylamino group, an ureido group, an alkoxy group, an amino group or an anilino group, into a silver halide emulsion layer of a color photographic light-sensitive material. Also, the 4-position of the 2-pyrazol-5-one can be substituted with a group which is released on coupling with the oxidation product of an aromatic primary amino color developing agent.

DETAILED DESCRIPTION OF THE INVENTION

Suitable couplers of the present invention include compounds represented by the following general formula (I):

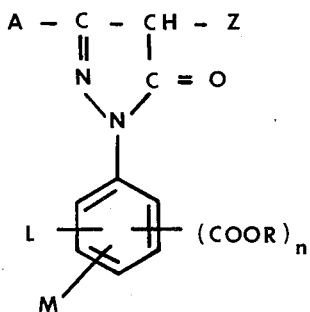

(I)

wherein n represents 1 or 2; R represents a straight-chain or branched-chain alkyl group, an alkenyl group or an aralkyl group, with each of the groups having about 8 to 26 carbon atoms when n is 1 (e.g., a straight-chain or branched-chain alkyl group such as octyl, 2-ethylhexyl, decyl, dodecyl, hexadecyl, octadecyl, etc., group, an alkenyl group such as an oleyl, etc., or an aralkyl group such as a benzyl, phenethyl, p-dodecylphenethyl, p-dodecyloxyphenethyl, etc.), and with each of the groups, which may be the same or different, having about 4 to 18 carbon atoms when n is 2 (e.g., a straight-chain or branched-chain alkyl group such as butyl, hexyl, octyl, 2-ethylhexyl, decyl, dodecyl, hexadecyl, octadecyl, etc., an alkenyl group such as an oleyl, etc., or an aralkyl group such as a benzyl, phenethyl, p-dodecylphenethyl, p-decyloxyphenethyl, etc.), and these groups can substituted with, for example, a hydroxy group, an acyloxy group (e.g., an acetoxy, dodecylcarbonyloxy, benzoyloxy, etc. group), a sulfo group, a sulfonyloxy group, an amido group (e.g., an acetamido, butyramido, benzamido, etc. group), an alkoxy group (e.g., a methoxy, ethoxy, octyloxy, etc. group), an aryloxy group (e.g., a phenoxy, tolyloxy, naphthoxy, etc. group), and the like; L and M each represents a hydrogen atom, a halogen atom (such as, fluorine, chlorine, bromine, etc.), an alkyl group (e.g., having 1 to 8 carbon atoms, such as methyl, ethyl, etc.), an alkoxy group (e.g., having 1 to 8 carbon atoms, such as methoxy, etc.), a cyano group, a hydroxy group, an amido group (e.g., having 1 to 8 carbon atoms such as acetamido, butyramido, etc.) or a carboxy group; Z represents a hydrogen atom or a group which is released on coupling with the oxidation product of an aromatic primary amino color developing agent; and A represents an amino group (preferably an N-alkylamino group or an N,N-dialkylamino group containing 1 to about 12 carbon atoms, such as methylamino, butylamino, N,N-diethylamino, hexylamino, N,N-dibutylamino, etc.), an anilino group (preferably anilino groups containing up to about 12 carbon atoms, such as anilino, 2,4-dichloroanilino, 2,4-dimethylanilino, 2-chloro-5-acetylaminoanilino, 2-chloro-5-dimethylsulfamoylanilino, 2-chloro-4-methoxycarbonylanilino, etc.), an acylamino group (preferably having up to about 12 carbon atoms, such as acetamido, butyramido, benzamido, 3-acetamidobenzamido, 3-butyramidobenzamido, etc.), an ureido group (preferably having up to about 12 carbon atoms, such as ureido, methylureido, butylureido, phenylureido, 3-acetamidophenylureido, 3-butyramidophenylureido, etc.), or an alkoxy group (preferably having 1 to about 12 carbon atoms, such as ethoxy, butoxy, etc.).

Of the magenta dye image-forming couplers according to the present invention of the general formula (I), the couplers represented by the following general formulae (II), (III) and (IV) are particularly useful

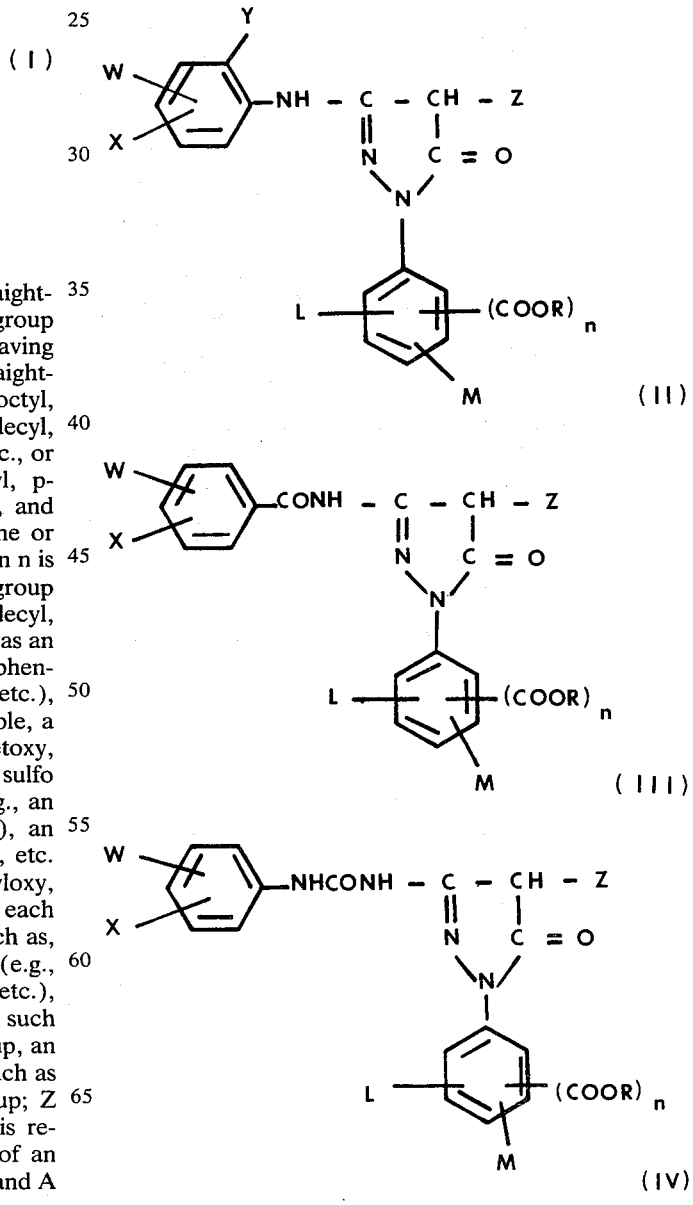

wherein n, R, L and M have the same meaning as defined in the general formula (I); W, X and Y, which may be the same or different, each represents an alkyl group (for example, having 1 to about 6 carbon atoms, such as methyl, ethyl, tert-butyl, etc.), an aryl group (for example, phenyl, tolyl, etc.), an alkoxy group (for example, having 1 to about 6 carbon atoms in the alkyl moiety thereof such as methoxy, ethoxy, etc.), an aryloxy group (for example, phenoxy, etc.), an alkylthio group (for example, having 1 to about 6 carbon atoms in the alkyl moiety thereof such as, methylthio, etc.), an amino group (for example, having 1 to about 6 carbon atoms in the alkyl moiety of the alkyl derivatives thereof such as ethylamino, dimethylamino, etc.), an amido group (for example, having 1 to about 6 carbon atoms in each acyl or sulfonyl moiety thereof such as acetamido, methylsulfonamido, diacylamino, etc.), a halogen atom (for example, fluorine, chlorine, bromine, etc.), a hydroxy group, a cyano group, a carboxy group, an alkoxycarbonyl group (for example, having 1 to about 6 carbon atoms in the alkoxy moiety thereof such as methoxycarbonyl, etc.), a carbamoyl group (for example, having 1 to about 6 carbon atoms in the alkyl moiety of the alkyl derivatives thereof, e.g. methylcarbamoyl, etc.), or a sulfamoyl group (for example, having 1 to about 6 carbon atoms in the alkyl moiety of the alkyl derivative thereof, e.g., diethylsulfamoyl, etc.), and X and W can also each represent a hydrogen atom; Z represents a hydrogen atom or a coupling releasable group such as a thiocyano group, an acyloxy group (for example, acetoxy, dodecanoyloxy, octadecanoyloxy, 3-n-pentadecylphenoxyacetoxy, benzoyloxy, β-naphthoyloxy, 3-[4-(2,4-di-tert-amylphenoxy)butyramido]benzoyloxy, etc.), an aryloxy group (for example, phenoxy, p-chlorophenoxy, p-nitrophenoxy, naphthoxy, etc.), a halogen atom (for example, chlorine, fluorine, etc.), an arylazo group (for example, a substituted or unsubstituted phenylazo or naphthylazo group, etc.), a 2-aryltriazolyl group (for example, 2-benzotriazolyl, 2-naphthotriazolyl, etc.), an alkylthio group (for example, an alkylthio group having 4 to 10 carbon atoms, etc.), an arylthio group (for example, phenylthio, 3-n-hexylamidophenylthio, naphthylthio, etc.), a heterocyclicthio group (for example, 2-benzothiazolylthio, 1-phenyl-5-tetrazolylthio, 2-benzoxazolylthio, 2-benzimidazolylthio, 5-phenyl-1,3,4-oxadiazolyl-2-thio, etc.), a cycloalkylthio group (for example, cyclohexylthio, etc.), a cycloalkoxy group (for example, cyclohexyloxy, etc.), an alkyloxycarbonyloxy group (for example, ethyloxycarbonyloxy, etc.), an aralkyloxycarbonyloxy group (for example, benzyloxycarbonyloxy, etc.), a sulfonamido group (for example, phenylsulfonamido, tolylsulfonamido, t-butylsulfonamido, etc.), an aliphatic amino group, an aromatic amino group, a diacylamino group (for example, phthalimido, succinimido, hydantoinyl, oxazolidinyl, etc.), a heterocyclic amino group (for example, piperidino, morpholino, imidazolino, etc.), and the like.

Of the magenta dye-forming couplers represented by the general formula (I), the compounds in which at least one of the ortho positions of the 1-phenyl group of the 2-pyrazol 1–5-one substituted with the group represented by L in the general formula (I) other than a hydrogen atom, in particular, the compounds in which the 1-phenyl group is represented by the following general formula (Va), are preferred.

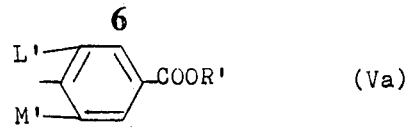

i.e., couplers of the general formula (V)

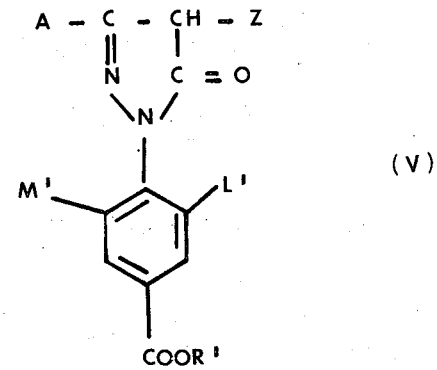

wherein L' and M', which may be the same or different, each represents a halogen atom (for example, fluorine, chlorine, bromine, etc.), an alkyl group (for example, having 1 to about 8 carbon atoms such as methyl, ethyl, etc.), an alkoxy group (for example, having 1 to about 8 carbon atoms in the alkyl moiety thereof such as methoxy, ethoxy, etc.) or a cyano group, and M' further represents a hydrogen atom; R' represents an alkyl group or an alkyl group substituted with an alkoxy group, an anyloxy group, an acyloxy group, an alkoxycarbonyl group, an acylamino group or a carbamoyl group, each having 8 to 26 carbon atoms. Examples of exemplary groups for L', M' and R' are those as described hereinbefore for L, M and R.

The magenta dye-forming couplers represented by the general formulae (I), (II), (III) and (IV) are characterized as having on the 1-phenyl group of 2-pyrazol-5-one, one or two carboxylic acid ester groups containing a specific number of carbon atoms which act as a hydrophobic group.

This hydrophobic group plays a role in rendering the coupler easily soluble in an organic solvent and easily dispersed into a hydrophilic colloid, preventing crystallization of the coupler in a photographic material, inhibiting the diffusion of the coupler in a photographic material, and the like. When the number carbon atoms of the hydrophobic group is too low, the coupler dissolves in a processing solution such as a developer solution and diffuses in a photographic material to adversely affect the color reproduction. On the other hand, when the number of carbon atoms is too high, there is another disadvantage in that the solubility of the coupler decreases due to an increase in the interaction between coupler molecules occur. Therefore the above described ranges of the number of carbon atoms are appropriate for the couplers of the present invention.

These hydrophobic groups include groups which are known in the art as ballasting groups. Specific examples of suitable ballasting groups are illustrated in the following.

1. Alkyl groups and alkenyl groups for example,

—$CH_2$-$CH(C_4H_9)_2$, —$C_{12}H_{25}$, —$C_{16}H_{33}$, —$C_{17}H_{33}$

2. Alkoxyalkyl groups for example,

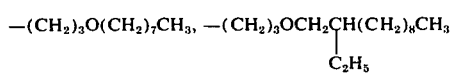

as described in Japanese Pat. Publication No. 27563/64

3. Aralkyl groups for example,

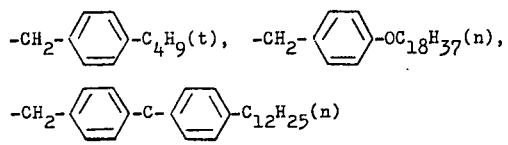

4. Alkylaryloxyalkyl groups for example,

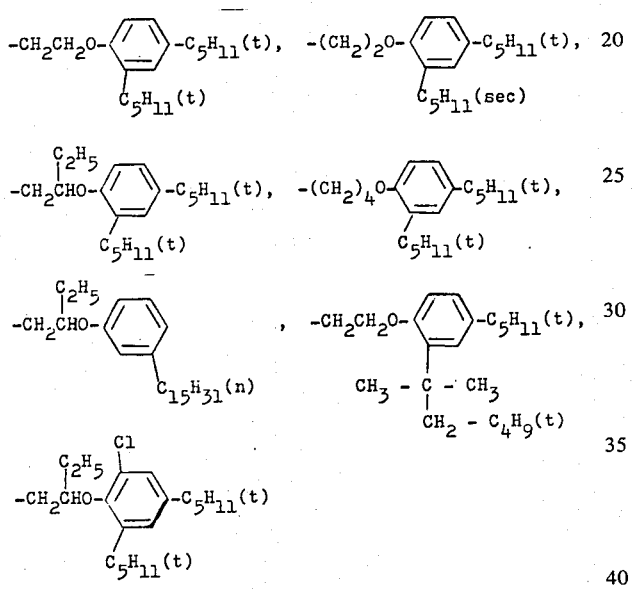

5. Acylamidoalkyl groups for example,

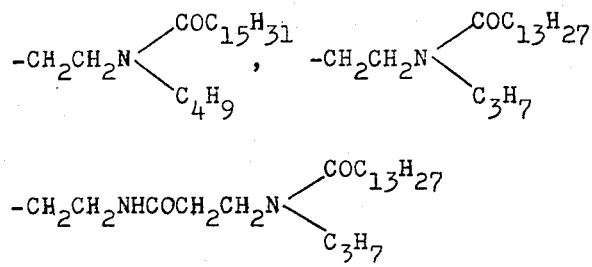

as described in U.S. Pat. Nos. 3,337,344 and 3,418,129.

6. Groups containing a long chain aliphatic group, such as an alkyl group or an alkenyl group, together with a water-solubilizing group such as a carboxy group or a sulfo group for example,

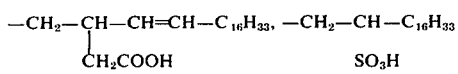

7. Alkyl groups substituted with an ester group for example,

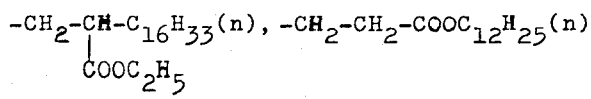

8. Aralkyl groups substituted with a aryl group or a heterocyclic group for example,

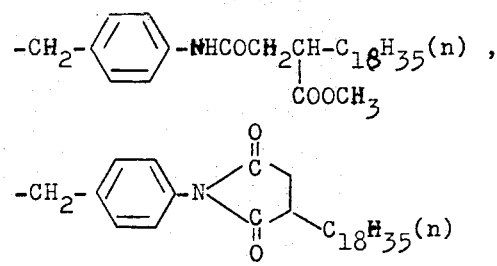

9. Aralkyl groups substituted with a aryloxyalkoxycarbonyl group for example,

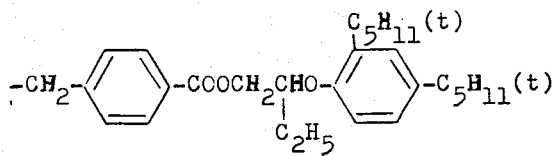

Couplers which contain a strongly hydrophilic group such as a carboxy group or a sulfo group can be incorporated into a photographic emulsion using an aqueous solution system.

The couplers represented by the above described general formula (II) are particularly preferred since magenta dye images formed from these couplers have excellent spectral absorption characteristics and good stability to humidity and heat.

The magenta couplers which can be used in the present invention include derivatives such as a 5-acyloxy pyrazole which is prepared by reacting a 2-pyrazol-5-one compound represented by the general formula (I) with an acylating agent, or an alkylidene-bis-(2-pyrazol-5-one) or an arylidene-bis-(2-pyrazol-5-one) which is prepared by reacting a 2-pyrazol-5-one compound with an aldehyde.

Magenta dye-forming couplers which can be used in the present invention are specifically illustrated below but the invention is not to be interprreted as being limited to only these couplers. Coupler (1): 1-(2,6-Dichloro-4-n-tetradecyloxycarbonylphenyl)-3-(2,4-dichloroanilino)-5-pyrazolone Coupler (2): 1-(2,6-Dichloro-4-n-tetradecyloxycarbonylphenyl)-3-(2-chloro-5-methoxycarbonylanilino)-5-pyrazolone Coupler (3): 1-{2,6-Dichloro-4-[β-(3-tert-butyl-4-hydroxyphenoxy)tetradecyloxycarbonyl]phenyl}-3-(2-chloro-5-acetamidoanilino-5-pyrazolone Coupler (4): 1-{2-Chloro-6-methyl-3-[β-(2,4-di-tert-amylphenoxy)ethoxycarbonyl]phenyl}-3-(2,5-dichloroanilino)-5-pyrazolone Coupler (5): 1-[2-Chloro-3,5-bis(n-octyloxycarbonyl)-phenyl]-3-(2,4-dichloroanilino)-5-pyrazolone Coupler (6): 1-(2,6-Dichloro-4-n-hexadecyloxycarbonylphenyl)-3-(2-chloro-5-ethylcarbamoylanilino)-5-pyrazolone Coupler (7): 1-(2,6-Dichloro-5-tetradecyloxycarbonylphenyl)-3-(2-methoxy-5-ethylsulfamoylanilino)-5-pyrazolone Coupler (8): 1-[2,6-dichloro-4-(4-n-tetradecanamidobenzyloxycarbonyl)phenyl]-3-(2,5-dichloroanilino)-5-pyrazolone Coupler (9): 1-(2,6-Dichloro-4-n-tetradecyloxycarbonylphenyl)-3-(2-chloro-4-methylsulfonylanilino)-5-pyrazolone Coupler (10): 1-{2,6-Dichloro-4-[(3-dodecyloxycarbonyl)-propoxycarbonyl]phenyl}-3-(2, 2,5-dichloroanilino)-5-pyrazolone Coupler (11): 1-(2,6-Dichloro-4-n-tetradecyloxycarbonylphenyl)-3-(2,4-dichloroanilino)-4-phthalimido-5-pyrazolone Coupler (12): 1-(2,6-Dichloro-4-n-hexadecyloxycarbonylphenyl)-3-(2-chloro-5-ethylcarbamoylanilino)-5-pyrazolonyl-(4) benzyl carbonic acid ester Coupler (13): 1-(2,6-Dichloro-4-n-tetradecyloxycarbonylphenyl)-3-(2,5-dichloroanilino)-4-(4-methoxyphenylazo)-5-pyrazolone Coupler (14): 1-(2,6-Dichloro-4-n-tetradecyloxycarbonylphenyl)-3-(2,4-dichloroanilino)-4-[(4-hydroxy-3-methylphenyl)-azo]-5-pyrazolone Coupler (15): 1-(2,6-Dichloro-4-n-tetradecyloxycarbonylpheyl)-3-(2-chloro-5-methoxycarbonylanilino-4-(1-phenyl-5-tetrazolythio)-5-pyrazolone Coupler (16): 1-(2,6-Dichloro-4-n-tetradecyloxycarbonylphenyl)-3-benzamido-5-pyrazolone Coupler (17): 1-(2,6-Dichloro-4-n-hexadecyloxycarbonylphenyl)-3-(2,5-dichlorobenzamido)-5-pyrazolone Coupler (18): 1-(2,6-Dichloro-4-n-tetradecyloxycarbonylphenyl)-3-(3-acetamidobenzamido)-5-pyrazolone Coupler (19): 1-{2,6-Dichloro-4-[β-(2,4-di-tert-amylphenoxy)butyloxycarbonyl]phenyl}-3-(4-cyanobenzamido)-5-pyrazolone Coupler (20): 1-(2,6-Dichloro-4-n-tetradecyloxycarbonylphenyl)-3-(3-acetamidobenzamido)-4-piperidino-5-pyrazolone Coupler (21): 1-(2,6-Dichloro-4-n-tetradecyloxycarbonylphenyl)-3-(3-phenylureido)-5-pyrazolone Coupler (22): 1-(2,6-Dichloro-4-n-hexadecyloxycarbonylphenyl)-3-[3-(3-acetamidophenyl)ureido]-5-pyrazolone Coupler (23): 1-{2,5-Dichloro-4-[β-(2,4-di-tert-amylphenoxy)ethoxycarbonyl]phenyl}-3-[3-(4-chlorophenyl)ureido]-5-pyrazolone Coupler (24): 1-(2,6-Dichloro-4-n-hexadecyloxycarbonylphenyl)-3-[3-(3-acetamidophenyl)ureido]-4-(4-methoxyphenylazo)-5-pyrazolone Coupler (25): 1-(2,6-Dichloro-4-n-tetradecyloxycarbonylphenyl)-3-(1-pyrrolidinyl)-5-pyrazolone Coupler (26): 1-(2,6-Dichloro-4-n-tetradecyloxycarbonylphenyl)-3-ethoxy-5-pyrazolone Coupler (27): 1-(2-Chloro-6-methoxy-4-tetradecyloxycarbonylphenyl)-3-(2,4-dichloroanilino)-5-pyrazolone The magenta dye-forming coupler used in the present invention can be prepared using various known methods. Specific examples of preparing typical couplers are shown below and other couplers can be prepared in a manner similar to the illustrated methods.

SYNTHESIS EXAMPLE 1

Preparation of 1-(2, 6-Dichloro-4-n-tetradecyloxycarbonylphenyl)-3-(2,4-dichloroanilino)-5-pyrazolone [Coupler (1)]

1. Preparation of 1-(2,6-dichloro-4-methoxycarbonylphenyl)-3-(2,4-dichloroanilino)-5-pyrazolone:

Method (a): A mixture of 9 g of ethyl 3,3-diethoxyacrylate prepared using the method of S. A. Glickman et al; JOURNAL OF THE AMERICAN CHEMICAL SOCIETY; Vol.67, page 1017 (1945) and 8 g of 2,4-dichloroaniline was heated at 120°–140°C for 2 hours under stirring in a nitrogen gas. The reaction product was distilled under reduced pressure to obtain 13 g of 3-(2,4-dichloroanilino)-3-ethoxyacrylate as an oil with a boiling point of 120°–135°C/1.5 mmHg. To this, 11 g of 2,6-dichloro-4-methoxycarbonylphenylhydrazine [Intermediate (h)] and 50 ml of acetic acid were added, and the mixture was refluxed for 2 hours. After distilling off the acetic acid from the reaction mixture, 30 ml of methanol was added, and the reaction product was allowed to stand to obtain the desired product. The melting point of the product was 188°–189°C.

Intermediate (h), 2,6-dichloro-4-methoxycarbonylphenylhydrazine, was prepared in the following manner.

2,6-Dichloro-4-methoxycarbonylaniline (melting point: 72°–74°C) was prepared by introducing two chlorine atoms into the anilino nucleus using the method of Cohen; J. CHEM. SOC.; Vol.81, Page 1336 (1902). The aniline was converted to 2,6-dichloro-4-methoxycarbonylphenylhydrazine in a sodium nitrites-tannous chloride system using the method of D. S. Tarbell et al; JOURNAL OF THE AMERICAN CHEMICAL SOCIETY; Vol.70, Page 1384 (1948). The melting point of the product was 130°–135°C.

Method (b): Preparation using the method described in U.S. Pat. No. 3,615,506. A mixture of 11 g of ethyl β-ethoxy-β-iminopropionate hydrochloride and 12 g of 2,6-dichloro-4-methoxycarbonylphenylhydrazine [Intermediate (h) used in Method (a) above] in 100 ml of methanol was stirred at room temperature for 1 hour. A solution containing 3g of metallic sodium dissolved in 50 ml of methanol was added dropwise to the mixture, and the mixture was further stirred at room temperature (about 20°–30°C) for 1 hour. After adding 15 ml of acetic acid, the reaction mixture was poured into 500 ml of water. The cyrstals formed were collected and recrystallized from methanol to obtain 11 g of 1-(2,6-dichloro-4-methoxycarbonylphenyl)-3-ethoxy-5-pyrazolone having a melting point of 101°–102.5°C. A mixture of 8 g of the 3-ethoxy-5-pyrazolone compound and 4 g of 2,4-dichloroaniline was heated to 140°C to form a uniform melt and after adding 1.4 g of methanesulfonic acid to the melt, the reaction was carried out at 140°–150°C for 3 hours with stirring while distilling off the ethanol formed. The reaction mixture was allowed to cool to 100°C and after adding 10 ml of methanol to dissolve the solid, the mixture was allowed to cool to room temperature to form cyrstals which were collected and recrystallized from methanol to obtain the desired compound. The melting point of the product was 132°–135°C and no lowering of the melting point was observed when it was melted together with 1-(2,6-dichloro-4-methoxycarbonylphenyl)-3-(2,4-dichloroanilino)-5-pyrazolone prepared by Method (a). The infrared spectra of both compounds were completely identical.

2. Preparation of 1-(2,6-dichloro-4-n-tetradecyloxycarbonylphenyl)-3-(2,4-dichloroanilino)-5-pyrazolone:

17.9 g of 1-(2,6-dichloro-4-methoxycarbonylphenyl)-3-(2,4-dichloroanilino)-5-pyrazolone was subjected to an exter exchange reaction by reaction with 9.3 g of 1-tetradecanol in the presence of 0.5 g of butyl titanate as catalyst using the method described in Japanese Pat. Publication No. 5582/67. The reaction product was recrystallized from ethanol to obtain the desired coupler, 1-(2,6-dichloro-4-n-tetradecyloxycarbonylphenyl)-3-(2,4-dichloroanilino)-5-pyrazolone as colorless cyrstals. The melting point of the product as 75°–77°C.

SYNTHESIS EXAMPLE 2

Preparation of 1-(2,6-Dichloro-4-n-tetradecyloxycarbonylphenyl)-3-benzamido-5-pyrazolone [Coupler (16)]

1. Preparation of 1-(2,6-dichloro-4-methoxycarbonylpheyl)-3-benzamido-5-pyrazolone:

A mixture of 27.5 g of ethyl β-ethyl-β-iminopropionate hydrochloride, 30 g of 2,6-dichloro-4-methoxycarbonylphenylhydrazine [Intermediate (h) as in Method (a) in Syntheses Example 1-(1)] and 11.5 g of anhydrous sodium acetate in 100 ml of methanol as stirred at room temperature for 2 hours. A solution containing 7 g of metallic sodium dissolved in 70 ml of methanol was added dropwise to the mixture, and the mixture was further stirred at room temperature for 2 hours. After adding 60 ml of acetic acid, the reaction mixture was poured into 1 liter of water. The crystals formed were collected and recrystallized from acetonitrile to obtain 21 g of 1-(2,6-dichloro-4-methoxycarbonylphenyl)-3-amino-5-pyrazolone having a melting point of 225°–229°C.

9 g of the 3-amino-5-pyrazolone compound described above and 8.4 g of benzoyl chloride were dissolved in 500 ml of acetonitrile. 6 g of triethylamine was added dropwise to the mixture and the mixture was refluxed for 3 hours. The reaction mixture was concentrated and 5 ml of methanol was added to the residue to yield 12 g of the diacetyl compound as white needles with a melting point of 201°–202°C.

10 g of the diacetyl compound was dissolved in 200 ml of methanol. To the solution 50 ml of triethylamine and 5 ml of water were added. The mixture was stirred at room temperature for 10 minutes, and excess acetic acid was added to the mixture under cooling with ice water to make the mixture acidic and then the mixture was poured into water. The crystals were collected by filtration and recrystallized from methanol to obtain 1-(2,6-dichloro-4-methoxycarbonylpheyl)3-benzamido-5-pyrazolone having a melting point of 234°–236°C. 2. Preparation of 1-(2,6-dichloro-4-n-tetradecyloxycarbonylphenyl)-3-benzamido-5-pyrazolone:

1-(2,6-Dichloro-4-methoxycarbonylphenyl)-3-benzamido-5-pyrazolone prepared by the method as described in step (1) was reacted with 1-tetradecanol in the presence of butyl titanate as catalyst in a manner similar to Synthesis Example 1 to obtain the desired coupler, 1-(2,6-dichloro-4-n-tetradecyloxycarbonylphenyl)-3-benzamido-5-pyrazolone as colorless crystals. The melting point of the product as 146°–147°C.

Since the magenta dye-forming couplers used in the present invention have high coupling reactivity and sufficient solubility in organic solvents, the color photographic materials produced using these couplers have good photographic properties such as sensitivity and gradation and can also be produced easily. In addition, the color photographic images obtained by developing color photographic materials containing these couplers have preferred spectral absorption characteristics for color reproduction and sufficient fastness and can be stored for a long period of time even under severe conditions.

In particular, the magenta couplers represented by the above-described general formula (II) can produce azomethine dyes which have excellent spectral absorption characteristics with less undesirable absorption of red light and blue light, and therefore they can be used to provide color photographic materials which reproduce a clear and bright red color and blue color. Furthermore the change of the spectral absorption characteristics of the dye images formed therefrom is much less when the amount of a non-volatile high-boiling organic solvent incorporated into a photographic emulsion layer is reduced. Thus, the ability to reduce the amount of the solvent for the coupler is not restricted and this is extremely advantageous in that the thickness of the photographic emulsion layer can be thinner.

The magenta dye images obtained from the magenta couplers represented by the general formula (II) have good fastness to heat and moisture, and do not require a treatment with a stabilizing agent such as formaldehyde, etc., and thus the development procedures can be simplified overall, which is one of the advantages of the present invention.

The couplers used in the present invention can be incorporated into a photographic emulsion using various techniques but typical examples are illustrated below.

a. A coupler is dissolved in an organic solvent which is sparingly soluble in water and has a high boiling point (higher than about 200°C), the coupler solution is dispersed in an aqueous medium, and the dispersion is added to a photographic emulsion. Examples of organic solvents suitable for this method are dibutyl phthalate, tricresyl phosphate, N,N-diethylcaproic acid amide, p-n-nonylphenol, 2-methyl-4-octylphenol, acetyltributyl citrate, tributylglyceride, etc.

b. A coupler is dissolved in a solvent which is comparatively less soluble in water and has a low boiling point, the coupler solution is dispersed in an aqueous medium, and the dispersion is added to a photographic emulsion. The organic solvent used is removed during the production of the photographic materials. Examples of solvents suitable for this method are ethyl acetate, cyclohexanone, β-n-butylethoxyethyl acetate, etc.

c. A coupler is dissolved in an organic solvent which is miscible with water and the coupler solution is incorporated in a photographic emulsion. The coupler is dispersed in the photographic emulsion as fine colloidal particles. The organic solvent used can be removed during the production of the photographic material or can be allowed to remain in the photographic emulsion layer after the production of the photographic material. Examples of solvents suitable for this method are dimethylformamide, dimethylsulfoxide, N-methylpyrrolidone, glycerol, tetrahydrofuran, etc.

The solvents used in the above-described methods (a), (b) and (c) can be used as mixtures if desired, from the standpoint of the solubility of the coupler to improve the degree of dispersion of the coupler. Also, a coupler can be incorporated into a photographic emulsion by a method similar to the aqueous solution system. That is, a coupler is dissolved in a solvent mixture which is prepared by mixing the solvent used in the method (c) and water, and adding a base such as sodium hydroxide, and the aqueous solution thus prepared is added to a photographic emulsion. A coupler having a water-solubilizing group such as a carboxy group is particularly suitable for this method.

For producing the silver halide color photographic lightsensitive materials using the magenta couplers of the present invention, the coupler represented by the general formula (I.) of the present invention can be used individually or as a mixture of two or more couplers or they can be used together with magenta dye-forming coupler or couplers other than the couplers represented by the general formula (I.) Suitable examples of magenta couplers other than the couplers represented by the general formula (I) are described in, e.g., U.S. Pat. Nos. 2,600,788, 2,983,608, 3,006,759, 3,062,653, 3,127,269, 3,214,437, 3,227,554, 3,227,550, 3,253,924, 3,311,476, 3,419,391, 3,419,808, 3,476,560, 3,558,319, 3,582,322, 3,615,506, 3,617,291, etc. Also the magenta coupler of the present invention can be used in the same photo. Graphic emulsion together with a magenta dye-forming coupler of the aqueous solution system. Furthermore, as described in Japanese Pat. Publication No. 391/65, the magenta coupler represented by the general formula (I) of the present invention can be used in a photographic emulsion containing a cyan coupler or a yellow coupler to improve the color reproducibility of color photographic light-sensitive materials.

The photographic emulsion containing the magenta coupler of the present invention can be applied to a conventional photographic support such as a film base or a baryta coated paper to provide various color photographic light-sensitive materials such as color positive films, color negative films, color reversal films, color printing papers, and the like. More specifically, suitable supports which can be used for the light-sensitive material of the present invention can be any of the supports known in the photographic art, for example, plastic films such as cellulose acetate, polycarbonate, polyethyleneterephthalate, polystyrene, baryta coated papers, polyethylenelaminated papers such as described in U.S. Pat. No. 3,253,922 or glass plates. A suitable coating amount of silver halide ranges from about $5 \times 10^{-2}$ mol/m² to about $1 \times 10^{-3}$ mol/m², preferably $2 \times 10^{-2}$ mol/m² to $3 \times 10^{-3}$ mol/m² of the support and a suitable amount of the coupler of the general formula (I) can range from about $5 \times 10^{-3}$ mol/m² to about $1 \times 10^{-4}$ mol/m², preferably $2 \times 10^{-3}$ mol/m² to $3 \times 10^{-4}$ mol/m² of the support.

In the above-described photographic emulsion a silver salt such as silver chloride, silver bromide, silver iodide, silver chlorobromide, silver chloroiodide, silver chlorobromoiodide, etc. can be used. Also, the so-called converted halide silver halide grains as described in U.S. Pat. No. 3,622,318 and British Pat. No. 635,841 can be used. The photographic emulsion can be sensitized using the natural sensitizers present in gelatin, a noble metal salt sensitizer, a reduction sensitizer, and the like. Suitable examples of chemical sensitizers are described in U.S. Pat. Nos. 1,547,944, 2,410,689, 2,399,083, 2,642,361, 2,487,850, 2,521,925, etc. Further the photographic emulsion can be optical sensitizer to provide appropriate spectral sensitivity to the photographic emulsion. Suitable examples of optical sensitizers are described in U.S. Pat. Nos. 2,519,001, 2,739,964, 3,481,742, 2,734,900, etc. Moreover, the photographic emulsion can contain an antifoggant, a stabilizer, an antistaining agent, an irradiation preventing dye, a gelatin plasticizer, a gelatin hardener, a coating aid, a polymer, and other conventional photographic additives.

It is preferred, for further increasing the stability of the color photograph obtained from the color photographic material of the present invention, that the color photographic light-sensitive material of the present invention contains a p-substituted phenol derivative together with the 2-pyrazol-5-one represented by the general formula (I).

Specific examples of p-substituted phenol derivatives suitable for the color photographic light-sensitive materials of the present invention are hydroquinone derivatives as described in U.S. Pat. Nos. 2,360,290; 2,418,613; 2,675,314; 2,701,197; 2,704,713; 2,728,659; 2,732,300; 2,735,765; 2,710,801 and 2,816,028, gallic acid derivatives as described in U.S. Pat. Nos. 3,457,079 and 3,069,262 and Japanese Pat. Publication No. 13469/68, p-alkoxyphenols as described in U.S. Pat. No. 2,735,767 and 3,698,909, and p-oxyphenol derivatives as described in U.S. Pat. Nos. 3,432,300; 3,573,050, 3,574,627 and 3,764,337. A suitable amount of the p-substituted phenol derivative which can be employed ranges from about 0.01 to about 10 mole per mole of the coupler, preferably 0.1 to 5 mole per mole of the coupler.

As a hydrophilic colloid which can be used in the photographic light-sensitive material of the present invention, for example, gelatin, a gelatin derivatives (such as acylated gelatin as described in U.S. Pat. No. 2,525,753, graft gelatin as described in U.S. Pat. No. 2,831,767, etc.), albumin, agar agar, gum arabic, a cellulose derivative (such as acetyl cellulose, hydroxyethyl cellulose, carboxymethyl cellulose, etc.), a synthetic resin (polyvinyl alcohol, polyvinyl pyrrolidone, polyacrylamide, etc.), and any other known hydrophilic colloid which can be used in the photographic art can be employed.

The hydrophilic colloid layer, in particular, a gelatin layer, containing the 2-pyrazol-5-one magenta coupler of the present invention can be hardened using various kinds of crosslinking agents. For example, an inorganic compound such as a chromium salt or a zirconium salt, an aldehyde type crosslinking agent such as mucochloric acid, 2,3-dihydroxy-1,4-dioxane, or 2-phenoxy-3-chloromalealdehydic acid as described in Japanese Pat. Publication No. 1872/71 can be effectively used in the present invention and a non-aldehyde type crosslinking agent such as a polyepoxy compound as described in Japanese Pat. Publication No. 7133/59, a poly(1-aziridinyl) compound such as bis(2,3-epoxypropyl)methyl propyl ammonium p-toluene sulfonate, 1,4-bis(2′,3′-epoxypropyloxy)butane, 1,3-diglycidyl-5-(γ-acetoxy-β-oxypropyl)isocyanurate, or those as described in Japanese Pat. Publication No. 8790/62 and an active halogen compound as described in U.S. Pat. Nos. 3,362,827 and 3,325,287 are particularly useful in the practice of the present invention.

The photographic light-sensitive materials containing the magenta coupler of the present invention can be processed using conventional methods. That is, after exposure, the photographic material can be developed in a developer solution containing a p-phenylenediamine type developing agent and then bleached and fixed to provide a color image having excellent spectral absorption characteristics and sharpness. Typical examples of the developing agents suitable for developing the color photographic light-sensitive materials of the present invention are 4-(N,N-diethylamino)aniline, 4-[N-ethyl-N-(22-methanesulfonamidoethyl)amino]-2-methylaniline, 4-[N-ethyl-N-($\beta$-hydroxyethyl)amino]-2-methylaniline, 4-(N,N-diethylamino)-2-methylaniline, and the like.

Specific examples of the present invention are described below but the present invention is not intended to be interpreted as being limited to these examples. Unless otherwise indicated, all parts, percentages, ratios and the like are by weight.

EXAMPLE 1

A solution prepared by heating at 60°C a mixture of 5 g of Coupler (16) of the present invention, 4 ml of tricresyl phosphate and 10 ml of ethyl acetate was added to 50 ml of an aqueous containing 5 g of gelatin and 0.15 g of sodium dedecylbenzene sulfonate at 60°C and then the mixture was stirred using a homogenizer to provide a coupler dispersion. The coupler dispersion was mixed with 100 g of a photographic emulsion containing $5.6 \times 10^{-2}$ mol of silver chlorobromide (silver chloride 50 mol %) and 10 g of gelatin and 5 ml of a 3% acetone solution of triethylene phosphoramide as a hardening agent was added thereto and finally the pH of the mixture was adjusted to 6.5. The mixture was coated on a cellulose triacetate film base and dried (dry thickness of the coated layer was 3.2 microns). The color photographic film thus prepared was exposed in a conventional manner and subjected to the following processing to provide a clear magenta dye image having an absorption maximum at 551 m$\mu$.

| Processing Step | Temperature | Time | |
|---|---|---|---|
| 1. Color Development | 21°C | 14 | minutes |
| 2. Washing | '' | 30 | seconds |
| 3. First Fixing | '' | 4 | minutes |
| 4. Washing | '' | 4 | minutes |
| 5. Bleaching | '' | 8 | minutes |
| 6. Washing | '' | 4 | minutes |
| 7. Second Fixing | '' | 4 | minutes |
| 8. Washing | '' | 6 | minutes |

The compositions of the processing solutions used were as follows.

| Color Developer Solution | |
|---|---|
| 4-(N,N-Diethylamino)-2-methylaniline Hydrochloride | 2.5 g |
| Sodium Sulfite (anhydrous) | 10 g |
| Sodium Carbonate (monohydrate) | 47 g |
| Potassium Bromide | 2 g |
| Water to make | 1 liter |
| | (pH 10.5) |
| Fixing Solution | |
| Sodium Thiosulfate (hexahydrate) | 80 g |
| Sodium Sulfite (anhydrous) | 5 g |
| Borax | 6 g |
| Glacial Acetic Acid | 4 ml |
| Potassium Alum | 7 g |
| Water to make | 1 liter |
| | (pH 4.5) |
| Bleaching Solution | |
| Potassium Ferricyanide | 100 g |
| Potassium Bromide | 5 g |
| Boric Acid | 10 g |
| Borax | 5 g |
| Water to make | 1 liter |
| | (pH 7.2) |

EXAMPLE 2

A solution prepared by heating at 60°C a mixture of 4 g of Coupler (1) of the present invention, 0.4 g of 2,5-di-tertoctylhydroquinone, 0.4 g of 6,6'-dihydroxy-7,7'-dimethoxy-4,4',4'-tetramethyl-bis-2,2'-spirochroman, 20 ml of tricresyl phosphate and 13 ml of ethyl acetate was added to 50 ml of an aqueous solution containing 5 g of gelatin and 0.10 g sodium dodecylbenzene sulfonate at 60°C and the mixture was stirred using a homogenizer to provide a coupler dispersion. The coupler dispersion was added to 100 g of a photographic emulsion containing $4.7 \times 10^{-2}$ mol of silver chlorobromide (silver chloride 50 mol %) and 5 ml of a 3 percent acetone solution of triethylene phosphoramide as a hardening agent was added thereto and finally the pH of the mixture was adjusted to 7.0. The mixture was coated on a resin coated paper and dried (dry thickness of the coated layer was 2.7 microns).

The color printing paper thus prepared was exposed stepwise and subjected to the following processing.

| Processing Step | Temperature | Time |
|---|---|---|
| Color Development | 30°C | 4 minutes |
| Blixing | '' | 2 minutes |
| Washing | '' | 2 minutes |
| Stabilization | '' | 2 minutes |

The compositions of the processing solutions used were as follows:

| Color Developer Solution | |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 ml |
| Diethylene Glycol | 20 ml |
| 4-[N-Ethyl-N-(2-methanesulfonamidoethyl)amino]-2-methylaniline Sesquisulfate | 8 g |
| Water to make | 1 liter |
| Blixing Solution | |
| Ferric Salt of Ethylenediamine Tetraacetic Acid | 45 g |
| Ammonium Thiocyanate | 10 g |
| Sodium Sulfite | 10 g |
| Ammonium Thiosulfate (60%) | 100 ml |
| Tetrasodium Salt of Ethylenediamine Tetraacetic Acid | 5 g |
| Water to make | 1 liter |
| Stabilizer Solution | |
| Tartaric Acid | 10 g |
| Zinc Sulfate | 10 g |
| Sodium Metaborate | 20 g |
| Water to make | 1 liter |

A clear magenta dye image having an absorption maximum at 542 m$\mu$ was obtained. The magenta dye was extracted from the color image and purified by a column chromatographic method and then the spectral absorption characteristics thereof was measured in ethyl acetate. The results are shown in Table 1, in which the subsidiary absorption density (I), the density at a wave length of 60 millimicrons longer than the main absorption wave length (II) and the wave length width at a density of 0.5 (III), when the main absorption density is controlled to 1.0 are shown. From the results it can be understood that the coupler of the present invention provides a sharp color image having less undesirable absorption in the blue light region and the red light region.

Table 1

| Absorption Characteristics of Dye | | |
|---|---|---|
| I | II | III |
| 0.138 | 0.122 | 65 |

The sample processed using the above-described processing was stored for 1 week at 80°C, for 2 weeks at 60°C and 75% RH or for 2 weeks under exposure to a flourescent lamp through a filter which absorbed substantially all ultraviolet light having wave lengths shorter than 400 millimicrons and the density reduction (%) of the magenta dye image from the initial density was measured. The results obtained are shown in Table 2.

Table 2

| | Fastness of Dye Image Storage Conditions | | | | | |
|---|---|---|---|---|---|---|
| | 80°C for 2 Weeks | | 60°C, 75%RH for 2 Weeks | | Fluorescent Lamp for 2 Weeks | |
| Initial Density | 0.5 | 1.0 | 0.5 | 1.0 | 0.5 | 1.0 |
| Density Reduction (%) | 8 | 6 | 7 | 4 | 8 | 4 |

The coupler of the present invention provides a magenta dye image of excellent fastness as shown in Table 2 above.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material having a silver halide emulsion layer containing a magenta color-forming coupler represented by the general formula (II)

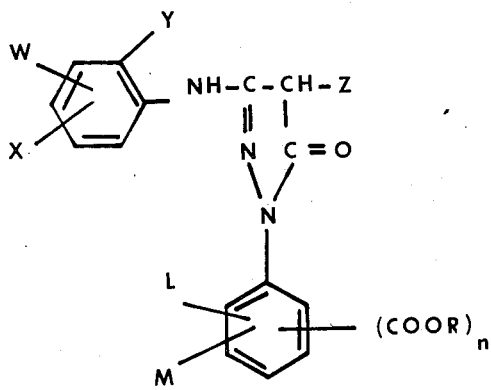

wherein n represents 1 or 2, R represents a straight-chain or branched chain alkyl group, an alkenyl group or an aralkyl group and when n is 1, R has about 8 to 26 carbon atoms and when n is 2, each R group has about 4 to 18 carbon atoms; L and M each represent a hydrogen atom, a halogen atom, an alkyl group, an alkoxy group, a cyano group, a hydroxy group, an amido group or a carboxy group; Z represents a hydrogen atom or a group which is released on coupling with the oxidation product of an aromatic primary amino color developing agent; W, X and Y each represent an alkyl group, an aryl group, an alkoxy group, an aryloxy group, an alkylthio group, an amino group, an amido group, a halogen atom, a hydroxy group, a cyano group, a carboxy group, an alkoxy carbonyl group, a carbamoyl group or a sulfamoyl group, and W and X each further represent a hydrogen atom.

2. The color photographic light-sensitive material as claimed in claim 1, wherein Z represents a hydrogen atom, a halogen atom, a thiocyano group, an acyloxy group, an aryloxy group, an arylazo group, a heterocyclic azo group, a 2-aryltriazolyl group, an alkylthio group, an arylthio group, a heterocyclic thio group, a cycloalkylthio group, a cycloalkoxy group an alkoxycarbonyloxy group, an aralkoxycarbonyloxy group, an aliphatic amino group, an aromatic amino group, a diacylamino group, or a heterocyclic amino group.

3. The color photographic light-sensitive material as claimed in claim 1, wherein said alkyl group, alkenyl group or aralkyl group for R is substituted with a hydroxy group, a halogen atom, a carboxy group, an alkoxycarbonyl group, an acyloxy group, a sulfo group, a sulfonyloxy group, an amido group, an alkoxy group or an aryloxy group.

4. The color photographic light-sensitive material as claimed in claim 1, wherein said magenta color forming coupler is represented by the general formula

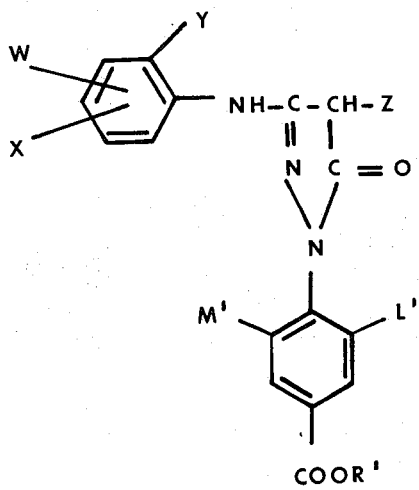

wherein W, X and Z have the same meaning as defined in claim 1; L' represents a halogen atom, an alkyl group, an alkoxy group, or a cyano group; M' represents a hydrogen atom, a halogen atom, an alkyl group, an alkoxy group or a cyano group; R' represents an alkyl group, or an alkyl group substituted with an alkoxy group, an aryloxy group, an acyloxy group, an alkoxycarboxyl group, an acylamino group or a carbamoyl group, each group having 8 to 26 carbon atoms.

5. The color photographic light-sensitive material as claimed in claim 1, where said magenta color forming coupler is: 1-(2,6-Dichloro-4-n-tetradecyloxycarbonylphenyl)-3-(2,4-dichloroanilino)-5-pyrazolone.

6. The color photographic light-sensitive material as claimed in claim 1, wherein said magenta color forming coupler is: 1-(2,6-Dichloro-4-n-tetradecyloxycarbonylphenyl)-3-(2-chloro-5-methoxycarbonylanilino)-5-pyrazolone.

7. The color photographic light-sensitive material as claimed in claim 1, wherein said magenta color forming coupler is: 1- 2-Dichloro-4-[β-(3-tert-butyl-4-hydroxyphenoxy)tetradecyloxycarbonyl]phenyl -3-(2-chloro-5-acetamidoanilino-5-pyrazolone.

8. The color photographic light-sensitive material as claimed in claim 1, wherein said magenta color forming coupler is: 1-(2,6-Dichloro-4-n-hexadecyloxycarbonylphenyl)-3-(2-chloro-5-ethylcarbamoylanilino)-5-pyrazolone.

9. The color photographic light-sensitive material as claimed in claim 1, wherein said magenta color forming coupler is: 1-(2,6-Dichloro-4-n-tetradecyloxycarbonylphenyl)-3-(2-chloro-4-methylsulfonylanilino)-5-pyrazolone.

* * * * *